US005749374A

United States Patent [19]

Schneider, Sr.

[11] Patent Number: 5,749,374

[45] Date of Patent: May 12, 1998

[54] PATIENT-TRANSPORT AND TREATMENT APPARATUS

[75] Inventor: Charles W. Schneider, Sr., Kalamazoo, Mich.

[73] Assignee: Cardi-Act, L.L.C., Plainwell, Mich.

[21] Appl. No.: 526,467

[22] Filed: Sep. 11, 1995

Related U.S. Application Data

[63] Continuation-in-part of Ser. No. 306,127, Sep. 14, 1994, Pat. No. 5,494,051.

[51] Int. Cl.$^{6}$ .......... A61F 5/37

[52] U.S. Cl. .......... 128/870; 5/600; 5/625; 5/658

[58] Field of Search .......... 128/845, 869, 128/870, 700; 5/621, 625, 626, 627, 628

[56] References Cited

U.S. PATENT DOCUMENTS

| | | | |
|---|---|---|---|
| 3,486,671 | 12/1969 | Sanders . | |
| 3,689,945 | 9/1972 | Laerdal . | |
| 3,986,505 | 10/1976 | Power . | |
| 4,033,000 | 7/1977 | Bonifay . | |
| 4,060,079 | 11/1977 | Reinhold | 5/627 |
| 4,768,241 | 9/1988 | Beney | 5/628 |
| 4,885,811 | 12/1989 | Hayes . | |
| 4,926,457 | 5/1990 | Poehner et al. . | |
| 4,987,623 | 1/1991 | Stryker et al. . | |
| 5,014,374 | 5/1991 | Williams . | |
| 5,018,226 | 5/1991 | Davies et al. . | |
| 5,117,521 | 6/1992 | Foster | 5/658 |
| 5,179,746 | 1/1993 | Rogers . | |
| 5,271,110 | 12/1993 | Newman . | |
| 5,292,094 | 3/1994 | VanKuiken . | |
| 5,343,869 | 9/1994 | Pross | 128/700 |

*Primary Examiner*—Michael A. Brown
*Attorney, Agent, or Firm*—Waters & Morse, P.C.

[57] ABSTRACT

The present invention is an improved portable litter for the transportation of a patient from the field to a hospital. The litter has devices for monitoring and responding to the condition of the patient, including blood pressure, temperature, blood oxygen, heart rate, and mass. At least one device for assisting the patient's breathing and for stabilizing the heart are provided with the litter. The litter can be folded to reduce its length and provide for ready maneuverability in constricted quarters. Electronic equipment provided with the litter includes an electronic central processing unit and a visual display to permit emergency personnel to maintain a close watch on the patient's condition, and for real-time communication with hospital personnel. The litter has provisions for connection with external air and electrical power, and has lights for operation under conditions of reduced illumination.

24 Claims, 3 Drawing Sheets

PATIENT-TRANSPORT AND TREATMENT APPARATUS

CROSS-REFERENCE TO RELATED APPLICATION

This is a continuation-in-part of my application Ser. No. 08/306,127, filed Sep. 14, 1994, now U.S. Pat. No. 5,494, 051, entitled Improved Patient-Transport Apparatus.

BACKGROUND OF THE INVENTION

1. Field of the Invention

This invention is in the field of medical apparatus. More specifically, the present invention is in the field of improved portable patient-transportation apparatus having means for providing supportive treatment to a patient or victim in the field, and forwarding record of that treatment from the field to a primary-care facility. This invention also comprises the method of use of the portable patient-transportation apparatus.

2. Description of the Prior Art

Apparatus for transporting patients to a primary-care facility are well-known in the art, including the emergency litter comprising two poles through the sleeves of two or more shirts as described in the Scout Handbook, and a hands-free means for carrying a litter described by Sanders in U.S. Pat. No. 3,486,671. Rogers describes a stretcher having wheels and patient-restraint means in U.S. Pat. No. 5,179,746; a patient can be strapped to a rigid back-board for immobilization, and the unit carrying the patient then rolled on its wheels to either directly to a care facility or to other transportation means for subsequent transfer to the care facility. Neither the Sanders nor the Rogers apparatus have any provision for treatment of a patient other than rudimentary first-aid prior to arrival at the care facility.

Apparatus such as that described by Reinhold in U.S. Pat. No 4,060,079 is a self-contained portable unit having parts relatively movable with respect to each other, such that the unit can be carried by one person to a location of limited accessibility; upon reaching the patient, an emergency crew can apply first aid, open the unit to accommodate the patient, and then transport the litter to appropriate transportation means, having the patient secured on the litter.

The '079 patent further describes the application of various treatments to the patient during transportation to a primary-care or other facility. This treatment includes a heart-lung resuscitator assembly, and has drug and equipment compartments for supporting oxygen containers and ancillary equipment for treatment of the patient. It has been found, however, that the Reinhold device, while useful for limited emergency cardiac-related treatment, is not suited for transporting a trauma victim while providing multiple types of supportive treatment.

Bucur, in U.S. Pat. No. 3,896,797, illustrates a partial litter, the purpose of which is to support the body of a victim undergoing cardiac stimulation. While a sturdier apparatus than that of Reinhold, the Bucur litter is not suitable for moving a victim undergoing emergency cardiac treatment, except for very short distances.

Newman describes a patient-transfer apparatus in U.S. Pat. No. 5,271,110 for moving a patient from one bed to another, or to a stretcher, litter or other transport means. The Newman apparatus, however, while useful for its described function, is too heavy for utility in field work, and is effectively limited to institutional functions in its application.

Other patents describing various methods of treating and transporting patients include Foster, U.S. Pat. No. 5,077, 843; Beney, U.S. Pat. No. 4,768,241; and Stith, U.S. Pat. No. 4,584,989. None of these describe apparatus capable of portability by a single person with a concomitant capability of treatment of the patient during transportation to a primary-care site.

One problem which emergency-room (ER) workers have heretofore encountered with respect to patients arriving therein after transportation from a remote site, with attendant emergency treatment prior to or during such transportation, has been a lack of dependable data regarding that treatment, or the response of the patient to whatever treatment was applied. Irrespective of significant levels of training in emergency treatment, and highly competent personnel, the very fact of the circumstances of the event can lend confusion to the situation; one emergency medical-service (EMS) worker may be seeking a pulse or treating a wound while another is moving debris, requesting bystanders to move, or performing any of a number of other functions. And while time is generally of the essence in a particular situation, that very fact can render it difficult or impossible to take note of the exact times involved, the job of keeping a patient alive or out of danger being the first priority.

On the arrival of the transport team at the ER, the recollections of the team members, while individually accurate, can suffer from an individual's viewpoint, time constraints and particular job function, requiring ER workers then to attempt to interpret and integrate that information in minimal time, in order properly to decide on the nature and extent of immediate treatment.

A possible method of overcoming the problem of fragmentary, confused or conflicting information would be to equip the transport device with recorders such as, e.g., a strip chart, for each mode of treatment protocol; thus, an oximeter could have a gauge for measurement of the oxygen ($O_2$) content of the patient's blood, a pulse monitor to determine pulse rate, and other measuring devices as appropriate, whether those devices be individual or integrated. However, this method still requires the ER physician or other attendant to read and interpret the strip chart or other recorded data to obtain necessary information upon the arrival of the EMS team at the ER.

SUMMARY OF THE INVENTION

The present invention is a patient-transport device having means for monitoring and responding to the condition of a patient under emergency treatment, comprising in combination a litter, at least one condition-monitoring means, treatment means, recording means, and remote-transmission means. One embodiment of the invention further comprises data-storage and -retrieval means, and data-recording and -transmission means. The litter is light enough to be portable, is configured to be portable by one person, and can be folded to permit its maneuvering in close quarters.

The method of this invention comprises providing emergency service to a patient at a site remote from a primary-care facility, comprising placing the patient on apparatus comprising a litter with a head end, a foot end, upstanding walls and a floor, and affixing to the patient means integral with or affixed to the litter for continuously monitoring and responding to the patient's vital signs prior to and during transport, wherein the litter has at least one power means connected with the monitoring and responding means.

This invention further comprises condition-responsive means for monitoring the vital signs and mass of the patient, the condition-responsive means providing input signals useful for guiding treatment of the patient.

DESCRIPTION OF THE PREFERRED EMBODIMENTS

The preferred embodiment of the present invention comprises portable apparatus for the treatment and transportation of a patient generally from a remote site to a primary-care facility, the apparatus having means for monitoring the weight and physical condition of the patient, comprising in combination a litter, condition-monitoring means, treatment means, recording means, and means for transmission of recorded data to a remote facility, where "remote" is defined for purposes of this specification as a health-care facility distant from the location of the litter. A more-preferred embodiment of the invention further comprises data-storage, data-retrieval, sound-recording and sound-transmission means. A most-preferred embodiment of this invention further comprises illumination means, a real-time chronometer, means for voice dialog with personnel at a remote facility, and means for determining the mass of the patient and the distribution of that mass.

The invention comprises patient-transport means, referred to herein as a litter, having affixed thereto or connected therewith a plurality of data-input and treatment devices, monitors to determine either or both of the extent of treatment or the condition of the patient, display means to permit observation of such monitoring, data-storage means, data-retrieval means, transmitting means, and a timing device. The design and construction of the apparatus of this invention are such that the apparatus is portable, wherein the term "portable" is defined for the purposes of this specification as being sufficiently light in weight to be carried by one person, and generally to be carried by two members of an EMS team when transporting a patient disposed thereon. The apparatus can be folded to permit easy maneuvering in constricted spaces.

Figure 1:
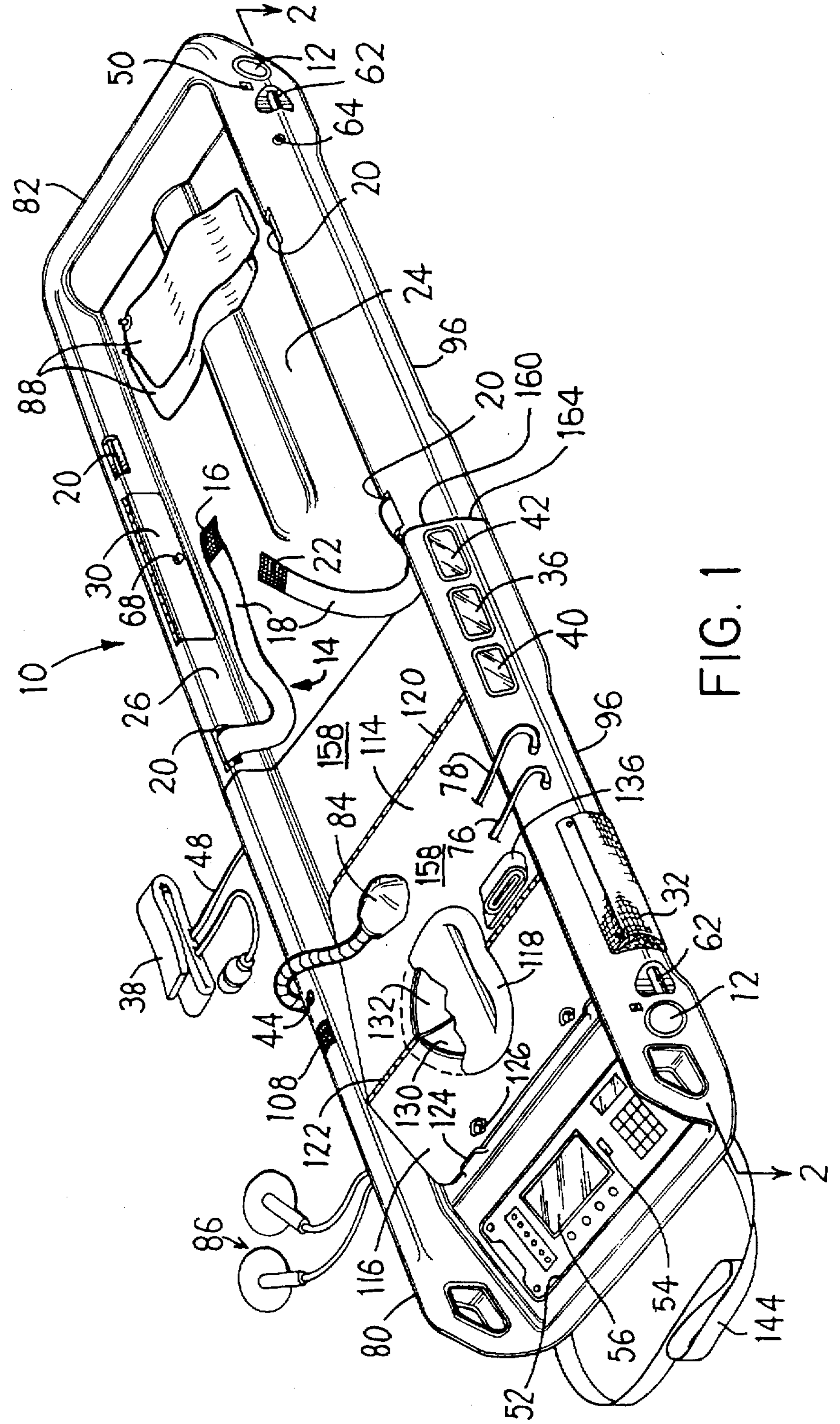
FIG. 1 is a view in perspective of the apparatus of the present invention.
Figure 2:
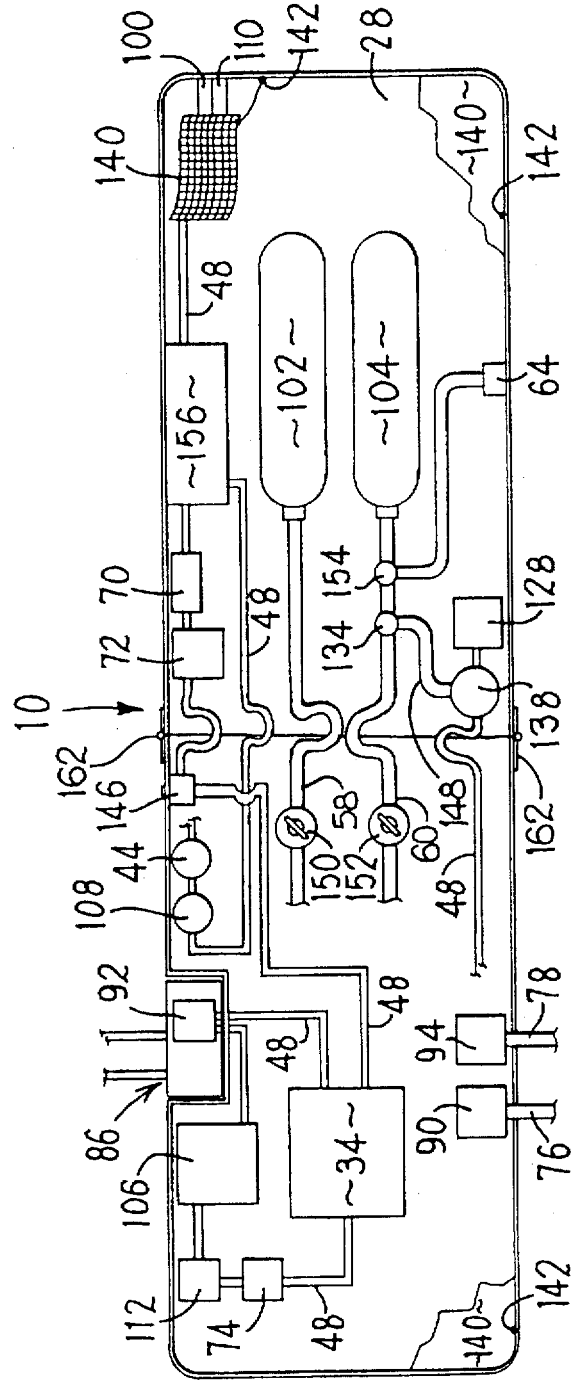
FIG. 2 is a sectional view taken along lines 2—2 of FIG. 1, showing disposition of moieties of the invention.
Figure 4:
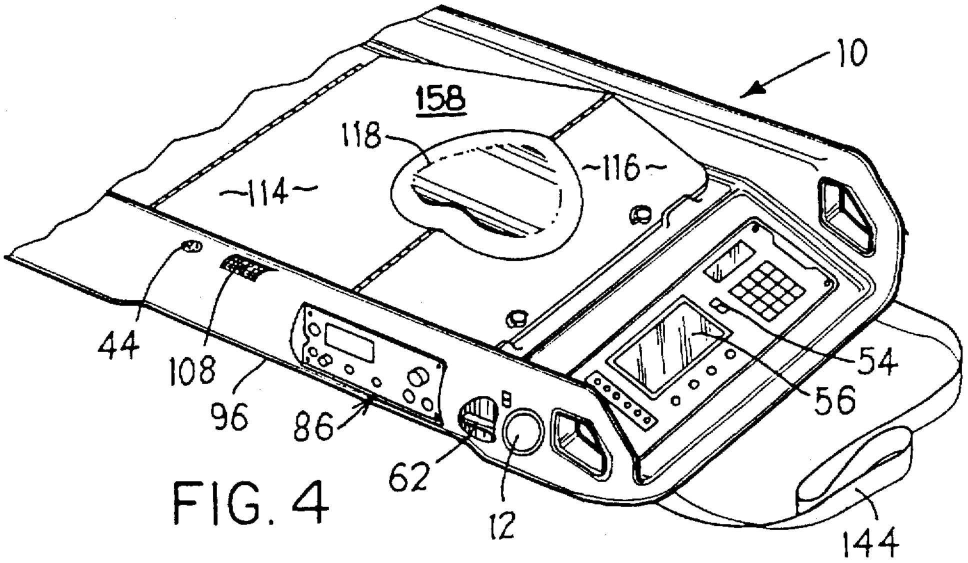
FIG. 4 is another view of the apparatus of the invention.

Turning now to the drawings, FIGS. 1 and 4 are perspective views from opposite sides of the present invention, showing litter 10 with illumination means 12 and removable defibrillator 86; FIG. 2 is a sectional view of litter 10, taken along lines 2—2 of FIG. 1, and shows the disposition of portions of the apparatus not visible in FIG. 1. Restraint means 14 are shown in FIG. 1 as at least one strap 18 passing over securement means shown as rods 20 rigidly affixed to wall 26 of litter 10, straps 18 having adjustment means 16 and fastening means 22 shown in FIG. 1 as hook and loop-pile fabric. The function of restraint means 14 is to keep the body of the victim from moving or falling off litter 10, either by inadvertence during transportation or due to bodily movement of the victim. Litter 10 has head end 80, foot end 82, floor 24, upstanding walls 26, and base 28 within which a patient or victim is disposed for treatment and transportation. Hinge means 160 in litter 10 provide the apparatus with the capability for being folded at right angles to its long axis, improving the portability or maneuverability of the apparatus, and making it easier for emergency personnel to maneuver the folded litter in constricted quarters such as through hallways, over stair rails, and the like.

Means for determining the patient's mass, shown in FIG. 1 as pressure-detecting film 158, is disposed on floor 24 and backrest 114 to provide data on the mass of the patient; by integrating the data secured from film 158, such as by means of appropriate programming through CPU 34, ER personnel can determine not only the patient's total mass, but the distribution of that mass as well, and can use the data in determining appropriate treatment. Pressure-detecting film, and the method for its use, can be obtained from, e.g., Sensor Products, Inc., 24 Castle Ridge Park, East Hanover, N.J. 07936-3547, U.S.A. Film 158 can be integral, or as shown in FIG. 1, can be disposed in sections in order to permit litter 10 to be folded; as noted, the data secured from the various portions can be integrated.

Fastening means 62 provide a method for affixing hooks, straps or other means for the purpose of, e.g., air rescue, particularly by helicopter, or for moving litter 10 vertically where necessary; fastening means 62 are preferably provided at the corners of litter 10.

Supplies and equipment for treatment or monitoring the condition of the patient can be disposed within storage means 30, shown in FIG. 1 as at least one compartment having closure means 68. The exact location of compartments 30 is not critical, it being adequate for purposes of this invention that they be easily accessible to EMS personnel. To keep stored items from abrasion, impact or other damage during handling of litter 10, compartments 30 and other enclosing location can be provided with an impact-absorbent material such as, e.g., a flexible vinyl or polyurethane foam. Flexible container 32, shown here as a mesh bag, provides retention for loose first-aid and other items such as, e.g., bandage strips, compresses, saline solution, and the like.

Display means 56 provide visual information concerning the patient's condition as reported by meters or monitors for any or all of, e.g., pulse rate 36, blood pressure 38, blood $O_2$ 40, body temperature 42, mass, and weight distribution as heretofore described.

At least one electronic data central processing unit (CPU) 34, shown in FIG. 2, is located at any convenient location within litter 10. CPU 34 is interconnected with, receives input from, and provides operating signals to the various sensors, treatment means and communication means, and display means 56 by any convenient connecting means, shown here as wires 48, although those skilled in the art will understand that other signal-transmission means can be used such as, e.g., suitably coded infra-red radiation. Display means 56 are preferably set in at least one recess 52 in litter 10, and can be disposed at any location convenient for observation by EMS attendants; this location can be at head end 80 or wall 26 of litter 10. Those skilled in the art will realize that display means 56 can be multiple; thus, display means 56 can be at head end 80 and either side 26, or foot end 82, of litter 10, or at each location.

Microphone 44 is connected through signal-transmission means, shown here as wires 48, to sound recorder 70, and data transmitter 72. Transmitter 72 preferably has multiple channels for the transmission of both voice and data. Those skilled in the art are aware that wireless means can also be used to transmit, among the instrumentation or other devices of the present invention, any of the various signals generated thereby.

Monitors 36, 38, 40 and 42 are interconnected by signal-transmission means 48 with data-recording and -storage means 74, shown in FIG. 2 as a recordable integrated-circuit chip. Those skilled in the art will realize that other means for data recording and retrieval can also be used, including, e.g., magnetic and optical media; it is sufficient that the data be capable of storage and retrieval on command, substantially without modification of the data so stored, i.e., without the introduction of non-data noise. Data so stored can include, without limitation, instrumental, sound, and visual data; the stored data can be transmitted simultaneously with storage, or retained in storage subject to recall upon command. The form of data storage can be analog or digital.

The sensors, monitors, operating moieties and recording devices are connected with CPU 34, which is interconnected with both data-recording and -storage means 74 and transmitter 72. The arrangement of routine data on the condition of the patient under treatment permits and provides rapid response as necessary to the condition of the patient; transmission of either or both data and voice to personnel at a remote primary-care facility; and dialog with such personnel as necessary and appropriate.

As depicted in FIGS. 1, 2 and 4, litter 10 preferably has removably affixed thereto and juxtaposed therewith at least the following items and devices: breathing-assistance means 84; defibrillator means 86; monitors for pulse rate 36, blood pressure 38, $pO_2$ 40, body temperature 42, and the mass, and mass distribution, of the patient; hyperbaric sleeves 88, and routine first-aid materials in bag 32 as discussed hereinabove. Tubing 76 provides flow for intravenous or other liquid treatment by infusion pump 90, and tubing 78 provides drainage or suction by suction means 94. Litter-support means 144 is shown here as a strap affixed to the litter to enable EMS personnel to bear the weight of litter 10 with a patient disposed thereon, while leaving their hands and arms free for prehension in rough or sloped terrain. Litter-support means 144 is preferably flexible and adjustable, to permit it to be disposed in the fashion most convenient for the person employing it.

The various removable monitoring and treatment means, such as breathing-assistance means 84; defibrillator means 86; monitors for pulse rate 36, blood pressure 38, $pO_2$ 40, and body temperature 42; are held in place on or in litter 10 by means well known in the art, such as quick-release or spring-loaded fittings. Where electrical connections are required for power or data transmission, plug-and-socket connectors can be used. Both the fittings and the connectors are well known in the art, and form no part of this invention as such.

Supporting and ancillary equipment, affixed to or within the structure of litter 10 in such fashion as to be removable or serviceable only by qualified personnel, include illumination means 12, pharmaceutical-infusion pump 90, suction means shown here as pump 94, $O_2$ supply comprising container 102 and air supply comprising container 104; power means such as, e.g., at least one battery 106, recording means 70, CPU 34, data-transmission means 72, and defibrillator-control means 92.

Litter 10 preferably has at least one auxiliary power source such as a backup battery 128 or turbine-driven generator 138 powered from either or both air cylinder 104 and external air. A solenoid valve 134 in hose 60 is maintained in the closed position with respect to generator 138 through hose 148 by current from battery 106 or 128; on failure of that current, valve 134 opens, and air from tank 104 causes generator 138 to turn, providing electrical energy to operate the systems until either battery 106 or 128 can be replaced.

If available, compressed air can replace or supplement air from tank 104 by connection to an external source of compressed air through connector 64 integral with litter 10 and air hose 66. Hose 66 is connected to hose 60 through valve 154. Valve 154 is a one-way valve, permitting air flow only into hose 60, in order to prevent inadvertent loss of air from tank 104.

Hose 58 serves to convey oxygen, and hose 60 serves to convey air, to ventilation or breathing-assistance apparatus 84, depending on the application. Hoses 58 and 60 are shown only partially, for clarity of presentation in FIGS. 1 and 2. Details of the connection of hoses 58 and 60 are well known to those skilled in the art, and form no part of this invention as such. Pressure-reduction valves 150 and 152 are placed in lines 58 and 60 to provide air and $O_2$ at pressures appropriate to their respective uses.

In illustration of the utility of the invention, litter 10 is preferably carried in an EMS vehicle, and draws standby and maintenance-charge power therefrom by connection through connection means 100 to external power such as a battery or household line circuit, well known to those skilled in the art, and forming no part of this invention as such. Upon removal of the apparatus from its storage position, switch 110 is triggered, turning on light 12 and causing elapsed-time meter 112 to start; real- and elapsed-time meter 112 is optionally integral with CPU 34. Each ancillary treatment apparatus or function is connected with elapsed-time meter 112 to provide a record of the clock time of operation and the duration of that operation. Thus, if infusion pump 90 is used to provide, e.g., 0.1N sodium bicarbonate solution to the patient, the times of that operation, any non-treatment intervals, and the total duration are recorded in data-storage means 74, and are thus available for review as necessary. Connection means 100 can further be used to connect to auxiliary electrical power in the field, as necessary.

Light 12 is preferably energized upon removal of litter 10 from its storage position, as noted hereinabove. Switch 50 is provided to enable light 12 to be turned off if necessary or appropriate. Light 12 is preferably juxtaposed within side handle 96 integral with the structure of litter 10, and can be protected from breakage by transparent shield means 98. Shield means 98 is preferably formed of translucent impact-resistant glass or plastic such as, e.g., polycarbonate, polyethylene terephthalate and the like. Light 12 can be multiple, and can be disposed at any one or more locations on litter 10. Side handle 96 is preferably multiple, and so situated as to provide convenience for lifting litter 10 by a plurality of EMS personnel when a patient is disposed on the litter.

To permit litter 10 to be carried quickly through, e.g., constricted spaces, the litter can be folded about hinge line 164 on hinge means 160. Upon arrival at the locus of the patient, litter 10 is returned to its normal conformation, and latch means 162, shown in FIG. 2, are engaged to prevent inadvertent movement of the portions of the litter with respect to each other. Referring again to FIG. 2, wires 48 and hoses 58 and 68 are provided with adequate length to permit their extension in the event it is necessary to fold litter 10 about hinge line 164.

Sound-recording means 70 is preferably of the type which responds to, and records, sounds above a pre-set level, thus avoiding the necessity of reviewing long stretches of non-data recording. Any member of the EMS team can effect the entry of relevant information by speaking above the pre-set sound level, e.g., "High blood-$CO_2$ level; starting oxygen at 0100 hours." In this fashion, the EMS attendants can continue rescue and aid efforts without stopping to turn on a recorder to accept dictation. Sound-recording means 70 can be equipped with an optional on-off switch 146, in order to enable recording on a full-time basis, or discontinue recording entirely, if appropriate.

Radio-reception and -transmission means 156 can be included, with microphone 44 and speaker 108 connected therewith, to permit dialog as necessary between EMS and ER personnel relating to patient treatment in the field. Data on the patient's condition and treatment can be transmitted to ER personnel as an adjunct to the voice transmission.

Display means 56 provides information for those functions generally required, such as, e.g., blood pressure, blood $O_2$ or $CO_2$, pulse rate, body temperature, and optionally the mass of the patient. The amount of $O_2$ or $CO_2$ in the patient's blood serves as a lung-function measurement, and provides a control parameter for metering $O_2$ to the patient through ventilation or breathing-assistance apparatus 84.

On operation of switch means 54, stored data can be displayed as required, including, e.g., battery, air and $O_2$ reserves, clock time, elapsed time from the time litter 10 was removed from its storage location, and the patient's vital signs and mass.

In order properly to position a patient if necessary for breathing assistance, optional backrest 114 and headrest 116, shown in FIG. 1, are juxtaposed on floor 24 of litter 10. Backrest 114 is affixed to floor 24, preferably by hinge means 120, and to headrest 116 by hinge means 122. Floor 24 is provided with stop means 124 to permit proper positioning of backrest 114.

Backrest 114 and headrest 116 are adjusted to conform to the patient's size because of the necessity of maintaining the appropriate angular relationship between the patient's torso and head to keep the tongue from blocking the airway, and for other reasons necessary to proper treatment. Backrest 114 is raised, and headrest 116 is set into the proper stop and secured there against inadvertent movement by lock means 126. Cushion 118 is secured to headrest 116, and serves both to maintain the head of the patient in optimal position and to avoid mechanical shock which might otherwise be transmitted through the body of litter 10 to the patient's head.

Both backrest 114 and headrest 116 have depressions 130 and 132 to accommodate the shape of the patient's head, thus facilitating the juxtaposition between the patient and floor 24 of litter 10. Restraint means 136 serves to maintain the head of the patient in the proper position for intubation, suction or any other reason. Preferred means include, e.g., an elastic band or an adjustable strap.

All of the components which might be subject to induced abberant currents or signals from strong electromagnetic-force fields including, e.g., lightning, radio broadcast signals, high-voltage and high-frequency devices, are shielded and grounded to avoid the introduction of spurious signals into such components. Thus, CPU 34 and wires 48 have shielding means 140 juxtaposed thereabout; shielding means 140 are electrically connected to ground-potential means 142. Shielding means 140 can further comprise electrical shielding generally, and are well-known to those skilled in the art, forming no part of this invention as such. It is sufficient that stray currents, voltages and electromagnetic signals be intercepted and negated without causing error in the data-gathering, -storage and -transmission devices of this invention.

Figure 3:
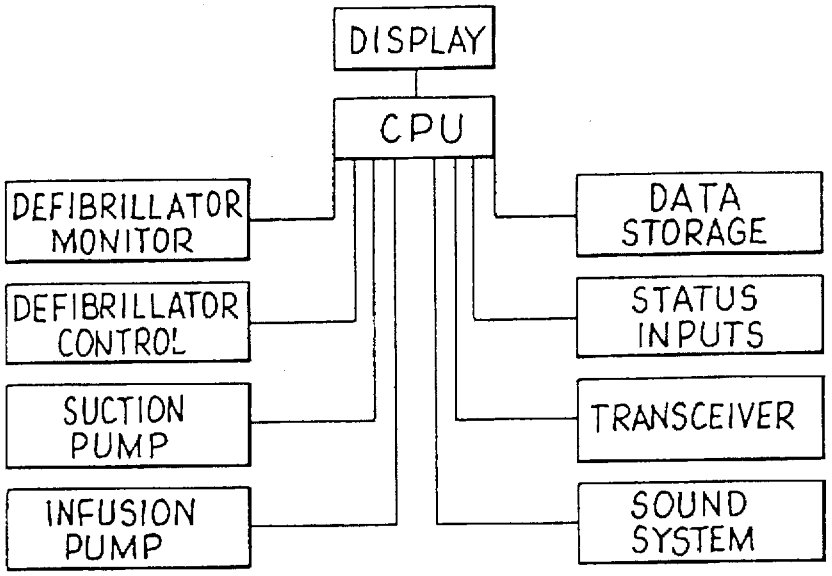
FIG. 3 is a block diagram of the most-preferred embodiment of the invention.

FIG. 3 presents a schematic representation of the operating mode of the present invention. The various moieties discussed hereinabove are shown as being connected with CPU 34, which is in turn connected with the display panel 56. As data are provided from data-storage unit 74, the CPU provides control of the various units as programmed. Data in storage unit 74 can be pre-programmed, entered in the field, or can result from input from any of the other moieties of the litter. Thus, e.g., input from blood-oxygen monitor 40 may indicate a relatively low level of oxygen in the patient's blood; the programming of CPU 34 then provides a command to increase the oxygen flow through breathing apparatus 84. The term "status inputs" in FIG. 3 is defined as the transmission of data to either or both data-storage unit 74 and to CPU 34, wherein the data are generated from any of the monitoring means, such as, e.g., blood-pressure monitor 38, body-temperature monitor 42 and the like, and provide information concerning the condition of the patient.

Modifications and improvements to the preferred forms of the invention disclosed and described herein may occur to those skilled in the art who come to understand the principles and precepts hereof. Accordingly, the scope of the patent to be issued hereon should not be limited solely to the embodiments of the invention set forth herein, but rather should be limited only by the advance by which the invention has promoted the art.

I claim:

1. A patient transport apparatus that is adapted to receive a patient from a remote location to support the patient to facilitate transporting the patient to a primary care medical facility, the apparatus comprising:

a portable patient transport litter with;

a monitor adapted to monitor and generate data responsive to the patient's vital signs, the monitor being connected with a data processing unit in the litter;

a data processing unit integrally mounted in the litter and connected with the monitor, the data processing unit being responsive to the monitor to receive and process the data; and a display integrally mounted in the litter and connected with the data processing unit, the display being responsive to the data processing unit to display the data.

2. The apparatus of claim 1, wherein the litter has a head portion that is adapted to receive and support at least the chest and head portions of the patient's body, and a foot portion that is adapted to receive and support at least the legs of the patient's body, and wherein the head and foot portions are hingedly interconnected to fold toward one another.

3. The apparatus of claim 1 having further a communication device that is integrally mounted in the litter, is operatively connected with the data processing unit, and is adapted to communicate at least the data with a predetermined remote location.

4. The apparatus of claim 3 wherein the communication device is adapted to transmit at least one of instrumental, sound, and visual data.

5. The apparatus of claim 1 further having a power source that is mounted in the litter and operatively connected with one of the monitor, the data processing unit, and the display.

6. The apparatus of claim 1 having a patient restraint that is adapted to secure the patient to the litter to restrain the patient from falling from the litter when the litter is pitched and rolled during transport.

7. The apparatus of claim 1, wherein the monitor comprises at least one device selected from the group consisting of a blood-oxygen meter, blood-pressure meter, pulse meter and lung-function meter.

8. The apparatus of claim 1 further comprising an electronic shield to minimize uncontrolled reception of electromagnetic energy by any of the monitor, the data processing unit, and the display.

9. The method of providing emergency service to a patient at a site remote from a primary-care facility, comprising the steps of:

providing a portable litter that is adapted to receive a patient from a remote location to support the patient to facilitate transporting the patient to a primary care medical facility;

providing a monitor that is integrally mounted in the litter and that is adapted to monitor and generate data responsive to the patient's vital signs;

providing a power source that is integrally mounted in the litter and that is connected with the monitor; and placing the patient on the portable litter.

10. The method of claim 9 wherein the litter has further affixed thereto at least one means for measuring the mass of a patient.

11. The method of claim 9 wherein the litter has further affixed thereto patient-ventilation apparatus.

12. The method of claim 9 wherein the litter has further affixed thereto an electronic data central processing unit.

13. The method of claim 9 wherein the litter has at least one electronic data central processing unit and display means interconnected with the monitoring and responding means.

14. The method of claim 9 further comprising at least one pharmaceutical infusion pump.

15. The method of providing emergency service to a patient at a site remote from a primary-care facility, comprising placing the patient on apparatus comprising a portable litter with a head end, a foot end, upstanding walls and a floor, and affixing to the patient means affixed to the litter for continuously monitoring and responding to the patient's vital signs prior to and during transport, wherein the litter has at least one power means connected with the monitoring and responding means, wherein the litter has further affixed thereto at least one means for measuring the mass of a patient, and wherein the means for measuring the mass of a patient comprises at least one pressure-detecting film.

16. In a method for providing emergency service to a patient at a site remote from a primary-care facility, the improvement which comprises in combination, the steps of:

providing a portable litter that is adapted to receive the patient from the remote location to support the patient to facilitate transporting the patient to the primary-care facility;

providing the litter with a monitor that is integrally mounted in the litter and that is adapted to monitor and generate data responsive to the patient's vital signs;

providing the litter with a pulmonary-ventilation device;

providing a power source that is integrally mounted in the litter and that is operatively connected with one of the monitor and the pulmonary-ventilation device; and placing the patient on the portable litter.

17. The method of claim 16 wherein the monitor comprises a data processing unit.

18. The method of claim 16 wherein the monitor is adapted to monitor one of the patient's blood-oxygen, blood pressure, pulse and lung-function.

19. The method of claim 16 further including the step of providing a container of oxygen that is mounted in the litter.

20. The method of claim 16 further including the step of providing the litter with electromagnetic-shielding means connected therewith.

21. The method of claim 16 further including the step of providing the litter with illumination means.

22. The method of claim 16 further including the step of providing the litter with a flexible litter-support means affixed thereto.

23. The method of claim 16 further including the step of providing the litter further an external power source connector.

24. An apparatus for transporting a patient comprising in combination:

a portable litter;

a patient-restraint affixed to the litter, the patient-restraint being adapted to secure the patient to the litter to restrain the patient from falling from the litter when the litter is pitched and rolled during transport;

a monitor integrally mounted in the litter, the monitor being adapted to monitor at least one of the patient's pulse, blood oxygen, blood pressure and heart rate prior to and during transport;

a display integrally mounted in the litter, the display being operatively connected with the monitor;

a data processing unit integrally mounted in the litter, the data processing unit being operatively connected with one of the monitor and the display;

a power integrally mounted in the litter, the power source being operatively connected with the one of the monitor, the display, and the data processing unit;

a communication device that is operatively connected with the data processing unit and that is adapted to communicate information with a remote location.

* * * * *